United States Patent
Hippalgaonkar et al.

(10) Patent No.: US 9,636,376 B2
(45) Date of Patent: May 2, 2017

(54) STABLE COMPOSITIONS OF PEPTIDE EPOXY KETONES

(71) Applicant: InnoPharma, Inc., Piscataway, NJ (US)

(72) Inventors: Ketan Hippalgaonkar, Highland Park, NJ (US); Kumaresh Soppimath, Monmouth, NJ (US); Satish Pejaver, Bridgewater, NJ (US); Navneet Puri, Bridgewater, NJ (US)

(73) Assignee: InnoPharma, Inc., New York, NY (US)

( * ) Notice: Subject to any disclaimer, the term of this patent is extended or adjusted under 35 U.S.C. 154(b) by 68 days.

(21) Appl. No.: 14/023,247

(22) Filed: Sep. 10, 2013

(65) Prior Publication Data

US 2014/0073583 A1    Mar. 13, 2014

Related U.S. Application Data

(60) Provisional application No. 61/699,752, filed on Sep. 11, 2012.

(51) Int. Cl.
*A61K 38/00* (2006.01)
*A61K 38/07* (2006.01)

(52) U.S. Cl.
CPC .................................. *A61K 38/07* (2013.01)

(58) Field of Classification Search
None
See application file for complete search history.

(56) References Cited

U.S. PATENT DOCUMENTS

| | | |
|---|---|---|
| 5,445,829 A | 8/1995 | Paradissis et al. |
| 7,737,112 B2 | 6/2010 | Lewis et al. |
| 8,263,578 B2 | 9/2012 | Soppimath et al. |
| 8,470,787 B2 | 6/2013 | Liu |
| 2009/0105156 A1* | 4/2009 | Phiasivongsa et al. ........ 514/18 |
| 2012/0052097 A1* | 3/2012 | Fetzer et al. .................. 424/400 |

FOREIGN PATENT DOCUMENTS

| | | |
|---|---|---|
| EP | 0215355 B1 | 4/1994 |
| EP | 1452097 B1 | 10/2007 |
| EP | 2083823 A2 | 1/2010 |
| WO | WO 2005/079604 A1 | 9/2005 |
| WO | WO 2013/112601 A1 | 8/2013 |

OTHER PUBLICATIONS

Fox and McSweeney, Advanced Dairy Chemistry vol. 3, Springer Science (2009).*
Jain et. al. Emerging role of carfilzomib in treatment of relapsed and refractory lymphoid neoplasms and multiple myeloma, Core Evidence 2011:6 43-57.*
PCT, PCT/US2014/054283, "The International Search Report," Dec. 18, 2014, 3 pages.
PCT, PCT/US2014/054283, "Written Opinion of the International Searching Authority," Dec. 18, 2014, 7 pages.

* cited by examiner

*Primary Examiner* — Jeanette Lieb
(74) *Attorney, Agent, or Firm* — Kristina L. Konstas

(57) ABSTRACT

The invention relates to pharmaceutical compositions that provide improved solubility and stability for peptide epoxy ketones. More specifically, the invention relates to pharmaceutical compositions comprising the peptide epoxy ketone proteasome inhibitor carfilzomib.

12 Claims, No Drawings

STABLE COMPOSITIONS OF PEPTIDE EPOXY KETONES

CROSS-REFERENCE TO RELATED APPLICATIONS

This application claims the benefit of U.S. Provisional Application No. 61/699,752, filed Sep. 11, 2012, the specification of which is hereby incorporated by reference in its entirety.

FIELD OF INVENTION

The present invention relates to pharmaceutical compositions comprising a peptide epoxy ketone, which can be a proteasome inhibitor, such as carfilzomib, wherein the pharmaceutical compositions provide improved stability and solubility for the proteasome inhibitor contained therein.

BACKGROUND OF THE INVENTION

Carfilzomib, which is the active ingredient in KYPROLIS®, is a peptide epoxy ketone proteasome inhibitor indicated for the treatment of patients with multiple myeloma who have received at least two prior therapies, including bortezomib and an immunomodulatory agent, and have demonstrated disease progression on or within 60 days of completion of the last therapy. Carfilzomib irreversibly binds to the N-terminal threonine-containing active sites of the 20S proteasome, the proteolytic core particle within the 26S proteasome. Carfilzomib has been shown to have antiproliferative and proapoptotic activities in vitro in solid and hematologic tumor cells. The compound has also been shown to inhibit proteasome activity in blood and tissue and delay tumor growth in models of multiple myeloma, hematologic, and solid tumors.

Peptide epoxy ketone proteasome inhibitors, such as carfilzomib, have proven difficult to formulate due to their low aqueous solubility. In addition, the proteasome inhibitors are very unstable. Thus, compositions comprising these compounds must typically be lyophilized before storage and reconstituted before use. Moreover, the reconstituted compositions are often not stable themselves (even under refrigerated conditions). As shown in Table 1, certain reconstituted KYPROLIS® compositions must be used within 24 hours after reconstitution because of their instability.

TABLE 1

| Storage Conditions of Reconstituted KYPROLIS | Stability*per Container | | |
|---|---|---|---|
| | Vial | Syringe | IV Bag (¶) |
| Refrigerated (2° C. to 8° C.; 36° F. to 46° F.) | 24 hours | 24 hours | 24 hours |
| Room Temperature (15° C. to 30° C.; 59° F. to 86° F.) | 4 hours | 4 hours | 4 hours |

*Total time from reconstitution to administration should not exceed 24 hours.
(¶) 5% Dextrose Injection, USP The need to lyophilize a composition comprising a peptide epoxy ketone proteasome inhibitor presents challenges to healthcare professionals. For example, dosing errors frequently occur during reconstitution of such products, and safety risks are presented if the reconstitution is not conducted aseptically. Additionally, the product after reconstitution is not stable for more than 24 hr, a product with such stability and storage temperature restrictions poses a problem for convenient use in a clinical use setting. Furthermore, lyophilized products allow for a one time reconstitution and use per patient. This type of presentation does not allow for injecting multiple doses. Also any unused portion of the reconstituted composition must be discarded, which leads to drug wasting. For at least these reasons, there is a need for new pharmaceutical compositions of peptide epoxy ketone proteasome inhibitors that provide improved solubility and stability for the peptide epoxy ketone proteasome inhibitor, as well as for ready-to-use compositions that eliminate the need for reconstitution.

SUMMARY OF THE INVENTION

Accordingly, in one aspect, the invention provides a lyophilized composition comprising a peptide epoxy ketone and a non-volatile sugar acid.

In one embodiment, the non-volatile sugar acid is lactobionic acid.

In one embodiment, the peptide epoxy ketone is a proteasome inhibitor.

In one embodiment, the peptide epoxy ketone is carfilzomib.

In one embodiment, the peptide epoxy ketone is carfilzomib and the non-volatile sugar acid is lactobionic acid.

The lyophilized pharmaceutical composition may be administered to a patient in need of such compositions after the composition is reconstituted with one or more pharmaceutically acceptable diluents.

In another aspect, the invention provides a pharmaceutical composition comprising (i) a peptide epoxy ketone; (ii) a solvent system comprising one or more water miscible pharmaceutically acceptable organic solvents suitable for injection, and optionally water; and (iii) a non-volatile sugar acid.

In one embodiment, the water miscible pharmaceutically acceptable organic solvent suitable for injection is selected from the group consisting of ethanol, propylene glycol, polyethylene glycol, glycerol, dimethylacetamide, N-methylpyrrolidone, dimethylsulfoxide, and mixtures thereof.

In one embodiment, the water miscible pharmaceutically acceptable organic solvent suitable for injection is selected from the group consisting of ethanol, propylene glycol, polyethylene glycol, and mixtures thereof.

In one embodiment, the non-volatile sugar acid is lactobionic acid.

In one embodiment, the peptide epoxy ketone is a proteasome inhibitor.

In one embodiment, the peptide epoxy ketone is carfilzomib.

In one embodiment, the peptide epoxy ketone is carfilzomib and the non-volatile sugar acid is lactobionic acid.

In one embodiment, the peptide epoxy ketone is carfilzomib; the non-volatile sugar acid is lactobionic acid; and the water miscible pharmaceutically acceptable organic solvent suitable for injection is selected from the group consisting of ethanol, propylene glycol, polyethylene glycol, and mixtures thereof.

In one embodiment, the pharmaceutical composition is a ready to use formulation.

In one embodiment, the pharmaceutical composition is a ready to dilute formulation.

The pharmaceutical compositions of the invention may also comprise one or more pharmaceutically acceptable excipients, such as a buffer, surfactant, antioxidant, preservative, isotonicity agent, and/or a lyoprotectant agent.

Another aspect of the invention relates to methods of making the pharmaceutical compositions discussed herein.

The pharmaceutical compositions of the invention overcome one or more limitations discussed above.

DETAILED DESCRIPTION OF THE INVENTION

The invention is generally directed towards pharmaceutical compositions comprising a peptide epoxy ketone.

In one embodiment, the composition is a lyophilized composition comprising the peptide epoxy ketone and a non-volatile sugar acid.

In one embodiment, the composition is a liquid formulation comprising (i) a peptide epoxy ketone; (ii) a solvent system comprising one or more water miscible pharmaceutically acceptable organic solvents suitable for injection, and optionally water; and (iii) a non-volatile sugar acid.

In each of the embodiments, the peptide epoxy ketone can be a proteasome inhibitor.

In each of the embodiments, the peptide epoxy ketone can be carfilzomib.

Where such compositions are lyophilized or concentrated above the concentration suitable for injection or infusion, the compositions will be administered after reconstitution with one or more pharmaceutically acceptable diluents.

Regardless of the particular form of the preparation, the pharmaceutical compositions contemplated herein may further comprise one or more buffers, surfactants, antioxidants, preservatives, isotonicity agents, and/or lyoprotectants.

Pharmaceutical compositions according to the instant disclosure provide improved stability and solubility for peptide epoxy ketones, such as carfilzomib.

Any recitation of ranges of values set forth below is merely intended to serve as a shorthand method of referring individually to each separate value falling within the range, unless otherwise indicated herein, and each separate value is incorporated into the specification as if it were individually recited herein. Furthermore, all references, including publications, patent applications, and patents, cited herein are hereby incorporated by reference to the same extent as if each reference were individually and specifically indicated to be incorporated by reference and were set forth in its entirety herein.

The terms "a" and "an" and "the," as used herein, are to be construed to cover both the singular and the plural, unless otherwise indicated herein or clearly contradicted by context.

The terms "comprising," "having," "including," and "containing," as used herein, are to be construed as open-ended terms (i.e., meaning "including, but not limited to,") unless otherwise noted.

The pharmaceutical compositions of the invention comprise at least one peptide epoxy ketone or a pharmaceutically acceptable salt thereof. Preferably, the peptide epoxy ketone is a proteasome inhibitor. Peptide epoxy ketones are epoxide-containing compounds, which contain a ketone group proximate to an epoxide group. Peptide epoxy ketones have the general structure:

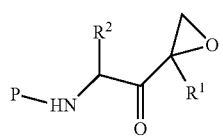

wherein:

$R^1$ and $R^2$ are hydrogen or a $C_1$-$C_8$ alkyl group, such as methyl, ethyl, propyl and butyl groups, which can be further substituted with one or more hydroxy, halogen, amino, carboxy, carbonyl, thio, sulfide, ester, amide, or $C_1$-$C_6$ alkoxy groups; and P is a peptide chain containing between 1 and 12 amino acids that is connected to the nitrogen by an amide bond with the carboxylic acid terminus of the amino acid. The N-terminal of the peptide chain may be protected or derivatized.

The stereochemistry of the carbons bonded to $R^1$ and $R^2$ can be (R) or (S). In one preferred embodiment the stereochemistry of the carbon bonded to $R^1$ and $R^2$ is as depicted below:

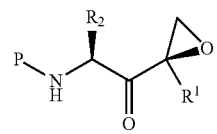

For some embodiments, the oxygen atom of the epoxide is configured as depicted above in order to facilitate interaction with an N-terminal nucleophilic group in an Ntn hydrolase. For example, irreversible interactions of enzyme inhibitors with the β5/Pre2 subunit of 20S proteasome, which lead to inhibition, appear to be facilitated by the configuration illustrated above. In the case of other Ntn hydrolases, the opposite stereochemistry of the epoxide may be preferred.

Preferably, the peptide chain contains two or more amino acids. In some embodiments, useful for inhibiting chymotrypsin-like (CT-L) activity of the proteasome, the peptide chain contains between two and eight amino acids, and in some preferred embodiments for CT-L inhibition, between two and six amino acids. In other embodiments useful for inhibiting the PGPH activity of the proteasome, the peptide chain contains between two and eight amino acids, and in some preferred embodiments for PGPH inhibition, between two and six amino acids. In other embodiments, the peptide chain contains between two and four amino acid units.

The amino acids can be a natural occurring essential amino acid, such as glycine, alanine, valine, isoleucine, leucine, phenylalanine, threonine, tyrosine, serine, and proline. The amino acids can be a naturally occurring non-essential amino acid, such as for example taurine, carnitine, citrulline, cystine, ornithine, norleucine, and others. The amino acids can also be a non-naturally occurring amino acid of general formula:

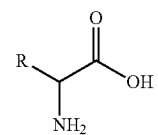

wherein the side chain, R, can be hydrogen, phenyl, or $C_1$-$C_8$ alkyl, wherein the $C_1$-$C_8$ alkyl can be further substituted with one or more phenyl, hydroxy, halogen, amino, carboxy, carbonyl, thio, sulfide, ester, amide, or $C_1$-$C_6$ alkoxy groups, and the phenyl can be further substituted with one or more hydroxy, halogen, amino, carboxy, carbonyl, thio, sulfide, ester, amide, or $C_1$-$C_6$ alkoxy groups.

Peptide epoxy ketones useful in the compositions of the invention include those described in U.S. Pat. No. 7,737,112, the content of which are incorporated herein by reference.

Most preferably, the peptide epoxy ketone proteasome inhibitor is carfilzomib (i.e., (2S)—N—((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide) which has the following structure:

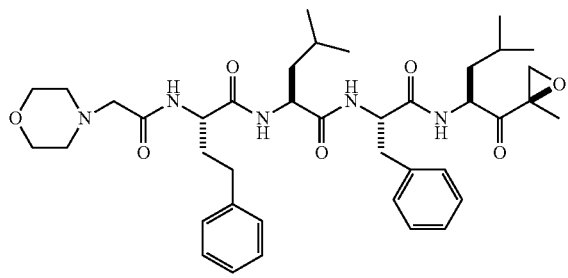 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

Lyophilized Compositions:

The lyophilized compositions of the invention comprise the peptide epoxy ketone and a non-volatile sugar acid. The peptide epoxy ketone may be a proteasome inhibitor. Preferably, the peptide epoxy ketone is carfilzomib.

The weight ratio of the non-volatile sugar acid to the peptide epoxy ketone ranges from about 2:1 to 15:1, preferably about 3:1 to 15:1, more preferably about 4:1 to 15:1, most preferably about 4:1 to 10:1. Typically, the weight ratio of the sugar acid to the peptide epoxy ketone is greater than 4:1, preferably greater than 5:1. Typically, the weight ratio of the sugar acid to the peptide epoxy ketone is less than 15:1, preferably less than 10:1.

In one embodiment, the lyophilized composition comprises about 60 mg of the peptide epoxy ketone and about 300 mg of the non-volatile sugar acid. In one embodiment, the lyophilized composition comprises about 60 mg of carfilzomib and about 300 mg of lactobionic acid. In one embodiment, the lyophilized composition comprises about 60 mg of carfilzomib and about 400 mg of lactobionic acid.

The phrase sugar acid means an oxidized derivative of sugar having one or more carboxylic acid functional groups. Sugar acids can be obtained by oxidizing the aldehyde group of a sugar. The term sugar includes any polyhydroxy carbohydrate moiety, including monosaccharides, disaccharides, polysaccharides. Preferably, the sugar acid is derived from a monosaccharide or a disaccharide. In one embodiment the sugar acid is a monosaccharide. In one embodiment the sugar acid is a disaccharide. The sugar acids may be used in the acid form or as a salt. When used as a salt, the salt is preferably a sodium, calcium, magnesium, or zinc salt. The sugar acid may be in the form of an ester or a lactone. Sugar acids also include compounds derived from amino sugars and acetylated amino sugars.

Non-volatile sugar acids useful in the compositions of the invention include, but are not limited to, N-acetylneuraminic acid, N-acetyltalosaminuronic acid, aldaric acid, aldonic acid, 3-deoxy-D-manno-oct-2-ulosonic acid, galaturonic acid, D-galacturonic acid, glucaric acid, gluconic acid, glucuronic acid, glucono-γ-lactone, glyceric acid, N-glycolylneuraminic acid, iduronic acid, isosaccharinic acid, lactobionic acid, mucic acid, muramic acid, neuraminic acid, pangamic acid, saccharic acid, sialic acid, threonic acid, ulosonic acid, uronic acid, X-Gluc, xylonic acid, ascorbic acid, and mixtures thereof. Preferably, the non-volatile organic acid is lactobionic acid.

Preferred sugar acids include, but are not limited to, gluconic acid, glucono-γ-lactone, lactobionic acid, glucuronic acid and its mono- or dilactones, pangamic acid, mannosaccharic acid and its mono- or dilactones, mucic acid and its mono- or dilactones, and mixtures thereof. Most preferred sugar acid is lactobionic acid.

The lyophilized compositions may further include one or more excipients suitable for inclusion in a lyophilized composition. For example, the lyophilized compositions may include a lyoprotectant. Suitable lyoprotectants include amino acids and polymers. Preferably, the amino acid is selected from the group consisting of lysine, alanine, and glycine. Suitable polymers include various proteins (e.g., gelatin and albumin), polyethylene glycol, gelatin, polyvinyl pyrrolidone, albumin, and Dextran-40. Typically the lyoprotectant represents less than 50% weight/weight of the lyophilized composition, and all concentrations above 1% weight/weight of the total composition are deemed effective to enhance the stability of the composition. In various embodiments, the lyoprotectant is present in an amount of at least about 5% weight/weight, at least about 10% weight/weight, or at least about 20% weight/weight of the total composition.

The compositions can be prepared by combining the peptide epoxy ketone, the non-volatile sugar acid, any optional excipients, and a suitable lyophilization solvent to provide a solution and then lyophilizing the solution using art-recognized lyophilization techniques.

The compositions can be sterilized. Sterilized compositions can be obtained using art-recognized methods for sterilization, such as filtration through 0.22 micron filters (e.g., PVDF filters), heat sterilization, radiation (e.g., gamma, electron beam, microwave), and/or ethylene oxide sterilization.

The non-volatile sugar acid compositions are more stable than a comparable composition that does not include the non-volatile sugar acid. Preferably the compositions have sufficient stability to allow storage at a commercially relevant temperature, such as between about 0° C. and about 60° C., for a commercially relevant period of time, such as at least one week, preferably at least one month, more preferably at least three months, and most preferably at least six months. In some embodiments the compositions have sufficient stability to allow storage at a commercially relevant temperature for more than one year, and in some embodiments more than two years. Stability can be measured using any physiochemical characterization techniques known to those skilled in the art, such as, for example high pressure liquid chromatography (HPLC).

The lyophilized pharmaceutical compositions discussed herein may be in a lyophilized powder or lyophilized cake form. Before use, the lyophilized pharmaceutical compositions are diluted or reconstituted with a pharmaceutically acceptable diluent. Any diluent known in the art in which the peptide epoxy ketone is soluble can be used. Preferably, the lyophilized composition is reconstituted with a solvent system so as to provide a liquid pharmaceutical composition as described below. In one embodiment, reconstitution provides a ready to use formulation as described below. In one embodiment, reconstitution provides a ready to dilute formulation as described below. The ready to dilute formulation can then be diluted with a suitable diluent before administration. Suitable diluents include, but are not limited to, water, saline, dextrose 5% in water, water for injection, and lactated ringer's solution. In one embodiment, the lyophilized composition is reconstituted directly with a suitable diluent.

The lyophilized pharmaceutical compositions are preferably contained in a vial or pre-filled syringe before reconstitution occurs.

It should be appreciated that the peptide epoxy ketone is present in the lyophilized pharmaceutical compositions in an amount that is suitable for administration after reconstitution.

Liquid Pharmaceutical Compositions:

The liquid pharmaceutical compositions of the invention comprise (i) a peptide epoxy ketone, (ii) a solvent system comprising one or more water miscible pharmaceutically acceptable organic solvents suitable for injection and optionally water, and (iii) a non-volatile sugar acid.

In one embodiment, the liquid pharmaceutical composition is a ready to use formulation. A ready to use formulation is a formulation that is suitable for administration without further dilution.

In one embodiment, the liquid pharmaceutical composition is a ready to dilute formulation. A ready to dilute formulation is a formulation that is suitable for administration after dilution with a suitable diluent.

The liquid pharmaceutical compositions can be a multi-dose formulation, i.e., a formulation that has a volume and/or quantity of the active pharmaceutical ingredient suitable for at least two independent and distinct administrations (to the same or a different patient) of the formulation.

The liquid pharmaceutical compositions are more stable than a comparable composition that does not include the non-volatile sugar acid. Without wishing to be bound by theory, it is believed that the sugar acid provides improved stability to the liquid pharmaceutical compositions. Importantly, the sugar acid also helps prevent the peptide epoxy ketone from precipitating when the liquid pharmaceutical composition is further diluted with a diluent. Thus, the liquid pharmaceutical compositions can advantageously be more readily diluted with a suitable diluent, without the peptide epoxy ketone precipitating. By reducing the tendency of the peptide epoxy ketone to precipitate, permits the preparation of more concentrated formulations to be obtained by diluting the by liquid pharmaceutical compositions.

The water miscible pharmaceutically acceptable organic solvent suitable for injection provides improved solubility for the peptide epoxy ketone compared to an aqueous composition in the absence of the pharmaceutically acceptable organic solvent. The pharmaceutically acceptable organic solvent also provides a solvent system that reduces degradation of the peptide epoxy ketone compared to an aqueous solvent in the absence of the organic solvent In one embodiment, the peptide epoxy ketone is a proteasome inhibitor. In one embodiment, the peptide epoxy ketone is carfilzomib.

Typically, the concentration of the peptide epoxy ketone in the liquid pharmaceutical composition ranges from about 0.1 to about 10.0 mg/mL. For example, the concentration of the peptide epoxy ketone in a ready to use formulation ranges typically from about 0.1 to about 3.0 mg/mL and the concentration of the peptide epoxy ketone in a ready to dilute formulation typically ranges from about 1.0 to about 10.0 mg/mL.

Any of the non-volatile sugar acids described above can be used in the liquid pharmaceutical compositions. The weight ratio of the non-volatile sugar acid to the peptide epoxy ketone ranges from about 2:1 to 15:1, preferably about 3:1 to 15:1, more preferably about 4:1 to 15:1, most preferably about 4:1 to 10:1. Typically, the weight ratio of the non-volatile sugar acid to the peptide epoxy ketone is greater than 4:1, preferably greater than 5:1. Typically, the weight ratio of the non-volatile sugar acid to the peptide epoxy ketone is less than 15:1, preferably less than 10:1.

Preferably, the non-volatile sugar acid is lactobionic acid.

Suitable water miscible pharmaceutically acceptable organic solvents suitable for injection are non-toxic organic solvents in which the peptide epoxy ketone is soluble. Suitable solvents include of ethanol, propylene glycol, polyethylene glycol, glycerol, dimethylacetamide, N-methylpyrrolidone, dimethylsulfoxide, and mixtures thereof. In one embodiment, the solvent is selected from the group consisting of ethanol, propylene glycol, polyethylene glycol, and mixtures thereof.

Preferably, the water miscible pharmaceutically acceptable organic solvent suitable for injection is selected from the group consisting of ethanol, propylene glycol, polyethylene glycol (in particular PEG 300 and PEG 400), and mixtures thereof.

The liquid pharmaceutical compositions may include water. Preferably the water miscible pharmaceutically acceptable organic solvent suitable for injection comprises more than about 25% by volume of the total amount of liquid used to formulate the pharmaceutical composition. More preferably, the water miscible pharmaceutically acceptable organic solvent suitable for injection comprises more than about 50% by volume of the total amount of liquid used to formulate the pharmaceutical composition. Most preferably, the water miscible pharmaceutically acceptable organic solvent suitable for injection comprises more than about 75% by volume of the total amount of liquid used to formulate the pharmaceutical compositions In one embodiment, the liquid pharmaceutical composition comprises at least two pharmaceutically acceptable solvents. The at least two pharmaceutically acceptable solvents can be present in any ratio.

In one embodiment, the liquid pharmaceutical composition comprises both ethanol and propylene glycol. Preferably, the volume ratio of ethanol to propylene glycol ranges from about 1:10 to 10:1. In one embodiment, the liquid pharmaceutical composition comprises ethanol, propylene glycol, and water. In one embodiment, the volume percent of the water ranges from 0% to about 60% of the total volume of liquid in the composition.

In one embodiment, the liquid pharmaceutical composition comprises both ethanol and polyethylene glycol (e.g., PEG 300 or PEG 400). Preferably, the volume ratio of ethanol to polyethylene glycol ranges from about 1:10 to 10:1. In one embodiment, the liquid pharmaceutical composition comprises ethanol, polyethylene glycol, and water. In one embodiment, the volume percent of the water ranges from 0% to about 60% of the total volume of liquid in the composition.

In one embodiment, the liquid pharmaceutical composition comprises carfilzomib; a solvent system comprising ethanol, propylene glycol, and water; and a non-volatile sugar acid.

In one embodiment, the liquid pharmaceutical composition comprises carfilzomib; a solvent system comprising ethanol, propylene glycol, and water; and lactobionic acid.

In one embodiment, the liquid pharmaceutical composition comprises carfilzomib in an amount of about 0.1 to 10 mg/mL; a solvent system comprising ethanol, propylene glycol, and water; and lactobionic acid. In one embodiment, the carfilzomib is present in an amount of about 1 to 5 mg/mL.

In one embodiment, the liquid pharmaceutical composition comprises carfilzomib in an amount of about 0.1 to 10 mg/mL; a solvent system comprising ethanol, propylene glycol, and water; and lactobionic acid, wherein the weight ratio of lactobionic acid to carfilzomib ranges from about 2:1 to about 15:1. In one embodiment, the carfilzomib is present in an amount of about 1 to 5 mg/mL.

In one embodiment, the liquid pharmaceutical composition comprises carfilzomib in an amount of about 0.1 to 10 mg/mL; a solvent system comprising ethanol, propylene glycol, and water; and lactobionic acid, wherein the weight ratio of lactobionic acid to carfilzomib ranges from about 2:1 to about 15:1, and the ratio of propylene glycol to ethanol is about 1:10 to 10:1 (v/v). In one embodiment, the ethanol and propylene glycol comprise more than about 25% by volume of the total amount of liquid used to formulate the pharmaceutical composition. In one embodiment, the ethanol and propylene glycol comprise more than about 50% by volume of the total amount of liquid used to formulate the pharmaceutical composition. In one embodiment, the ethanol and propylene glycol comprise more than about 75% by volume of the total amount of liquid used to formulate the pharmaceutical composition. In one embodiment, the carfilzomib is present in an amount of about 1 to 5 mg/mL.

In one embodiment, the liquid pharmaceutical composition comprises carfilzomib; a solvent system comprising ethanol, polyethylene glycol, and water; and a non-volatile sugar acid. In one embodiment, the polyethylene glycol is selected from PEG 300 and PEG 400.

In one embodiment, the liquid pharmaceutical composition comprises carfilzomib; a solvent system comprising ethanol, polyethylene glycol, and water; and lactobionic acid. In one embodiment, the polyethylene glycol is selected from PEG 300 and PEG 400.

In one embodiment, the liquid pharmaceutical composition comprises carfilzomib in an amount of about 0.1 to 10 mg/mL; a solvent system comprising ethanol, polyethylene glycol, and water; and lactobionic acid. In one embodiment, the polyethylene glycol is selected from PEG 300 and PEG 400. In one embodiment, the carfilzomib is present in an amount of about 1 to 5 mg/mL.

In one embodiment, the liquid pharmaceutical composition comprises carfilzomib in an amount of about 0.1 to 10 mg/mL; a solvent system comprising ethanol, polyethylene glycol, and water; and lactobionic acid, wherein the weight ratio of lactobionic acid to carfilzomib ranges from about 2:1 to about 15:1. In one embodiment, the polyethylene glycol is selected from PEG 300 and PEG 400.

In one embodiment, the liquid pharmaceutical composition comprises carfilzomib in an amount of about 0.1 to 10 mg/mL; a solvent system comprising ethanol, polyethylene glycol, and water; and lactobionic acid, wherein the weight ratio of carfilzomib to lactobionic acid ranges from about 2:1 to about 15:1, and the ratio of ethanol to polyethylene glycol is about 1:10 to 10:1 (v/v). In one embodiment, the ethanol and polyethylene glycol comprise more than about 25% by volume of the total amount of liquid used to formulate the pharmaceutical composition. In one embodiment, the ethanol and polyethylene glycol comprise more than about 50% by volume of the total amount of liquid used to formulate the pharmaceutical composition. In one embodiment, the ethanol and polyethylene glycol comprise more than about 75% by volume of the total amount of liquid used to formulate the pharmaceutical composition. In one embodiment, the carfilzomib is present in an amount of about 1 to 5 mg/mL.

The liquid pharmaceutical compositions of the instant invention may further comprise one or more excipients, such as, buffers, surfactants, antioxidants, preservatives, isotonicity agents, and/or lyoprotectants.

For instance, a buffer is typically used in the liquid pharmaceutical compositions of the invention to control the pH. As shown in Table 2, at least some peptide epoxy ketones (e.g., carfilzomib) have demonstrated a strong pH-dependent solubility.

TABLE 2

Effect of pH on Solubility of Carfilzomib

| pH | Saturation Solubility (µg/mL) |
| --- | --- |
| 1.7 (1% L-Cysteine) | 459.0 |
| 3.5 (15 mM Acetate Buffer) | 125.0 |
| 5.0 (15 mM Citrate Buffer) | 9.0 |
| 7.0 (15 mM Phosphate Buffer) | 5.0 |

Accordingly, a buffer may be used in the liquid pharmaceutical compositions of the instant invention to maintain a pre-selected pH level at which the peptide epoxy ketone is soluble.

Examples of suitable buffers include mixtures of a weak acid and alkali metal salt (e.g., sodium, potassium) and the conjugate base of the weak acid. Suitable buffers include, for example, buffers selected from the group consisting of citric acid, acetic acid, maleic acid, phosphoric acid, succinic acid, or tartaric acid, as well as the counter ion salts thereof. The molar concentration of the buffer typically ranges between about 5 millimolar and about 150 millimolar, and is most preferably about 15 millimolar. The buffer will typically have a pH of about 3.5, however, modifications to the pH value are also contemplated herein. It will be recognized by those of skill in the art that determination of the preferred solubility range of a peptide epoxy ketone around a pH of 3.5 using any of the aforementioned buffers can be performed using known techniques.

The pH level for each pharmaceutical composition should be selected to provide suitable solubility of the peptide epoxy ketone used therein. It is generally preferred, however, that the pH of the compositions be suitable for injection and, therefore, will typically be between about 2.0 and about 9.0, and even more typically between about 2.5 and about 8.0.

The liquid pharmaceutical compositions according the invention may also comprise an anionic, nonionic, cationic, or amphoteric surfactant. Anionic surfactants that may be used in the pharmaceutical compositions of the invention include alkyl ether sulfates and carboxylic acids, in particular in form of their alkali salts, as well as protein fatty acid condensates.

Examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester. Examples of such preferred polyoxyethylene derivatives of polyol esters include, but are not limited to PEG-80, sorbitan laurate, and Polysorbate 80.

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl gluocosides comprise from about 1 to about 6 glucose residues per molecule of alkyl glucoside. A preferred glucoside is decyl glucoside, which is the condensation product of decyl alcohol with a glucose polymer and is available commercially from Cognis Corporation of Ambler, Pa. under the tradename, "Plantaren 2000."

Various cationic surfactants may also be suitable for use in the present compositions. Examples of suitable cationic surfactants include, but are not limited to alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred.

Also possible is the incorporation of amphoteric surfactants, such as alkyl betaines, alkyl amido betaines, and alkyl amphoacetates.

To still further improve the stability, the liquid pharmaceutical compositions may also include one or more anti-oxidants. For example, hydrophobic anti-oxidants include butylated hydroxytoluene, butylated hydroxyanisole, propyl gallate, and α.-tocopherol, DL-tocopherol, α-tocopherol acetate, α-tocopherol Tocopherol Polyethylene Glycol Succinate (Vitamin E TPGS), L-cysteine, or hydrophilic anti-oxidants, including sodium EDTA and thioglycerol. Most typically, the concentration of the anti-oxidant will be between 0.005% and 5% weight/weight of the total composition.

Additionally, or alternatively, the contemplated liquid pharmaceutical compositions may include a preservative (e.g., phenol, thimerosal, chlorobutanol, benzyl alcohol, m-cresol, phenoxyethanol, methylparaben and propylparaben), typically at a concentration of between 0.001% weight/weight and about 5% weight/weight of the total composition, and is most typically between about 0.003% and about 2.0% weight/weight of the total composition.

The liquid pharmaceutical compositions contemplated herein may further include isotonicity agents and/or lyoprotectants. Suitable isotonicity agents include sodium chloride, glycerol, and thioglycerol. Suitable lyoprotectants are described above.

The liquid pharmaceutical compositions can be prepared according to a method comprising the steps:
(a) placing a desired amount of a peptide epoxy ketone in a compounding vessel;
(b) adding one or more water miscible pharmaceutically acceptable organic solvents suitable for injection to the compounding vessel;
(c) optionally adding water to the compounding vessel;
(d) mixing the contents of the compounding vessel;
(e) optionally adding one or more excipients to the compounding vessel;
(f) adding a non-volatile sugar acid to the compounding vessel; and
(g) mixing the contents of the compounding vessel until the non-volatile sugar acid is dissolved.

The contents of the compounding vessel may be sterilized using any known methods of sterilization, including filtration through 0.22 micron filters (e.g., PVDF filters), heat sterilization, radiation (e.g., gamma, electron beam, microwave), and/or ethylene oxide sterilization.

The pharmaceutical compositions of the instant invention are suitable for administration to mammals, including humans. When administered to humans, the compositions are typically administered by intramuscular, subcutaneous, intra-arterial, or oral routes.

Regardless of the particular composition, it is preferred that the composition is packaged in a container suitable for single or multi-use. Such containers include an ampoule, a vial, a pre-filled syringe, and an intravenous bag. Multi-use containers may contain the peptide epoxy ketone in an amount suitable to allow at least two distinct uses, more typically at least five distinct uses, and even more typically at least ten distinct uses (each use which may or may not require the same quantity of composition administered to the patient). Thus, preferred multi-use containers will be configured to contain a volume of the composition that is suitable for multiple and independent administrations. Such containers include vials with a rubber stopper that can be pierced with a needle of a syringe.

The following examples are presented for illustrative purposes only, and are not intended to limit the scope of the invention.

EXAMPLES

For each of the Examples described below, the following HPLC methodology was used to determine the relative retention time (RRT) of impurities in the compositions:
Mobile Phase A: 0.5 mL of TFA in 1000 mL of distilled water
Mobile Phase B: 100% HPLC grade Acetonitrile
Diluent: Acetonitrile:Water (1:1 v/v)
Elution program:

| Time Min | Flow mL | % A | % B |
|---|---|---|---|
| 0.01 | 1.00 | 95.0 | 5.0 |
| 5.00 | 1.00 | 90.0 | 10.0 |
| 10.00 | 1.00 | 85.0 | 15.0 |
| 38.00 | 1.00 | 20.0 | 80.0 |
| 40.00 | 1.00 | 0.0 | 100.0 |
| 43.00 | 1.00 | 0.0 | 100.0 |
| 45.00 | 1.00 | 95.0 | 5.0 |
| 50.00 | 1.00 | 95.0 | 5.0 |

Flow rate: 1.0 mL/min
Detector Wavelength: 210 nm
Injection volume: 10 micro liters
Run time: 50 min
Column: Waters Symmetry C18 (250×4.6 mm), 5 microns
Sample temperature: 5° C.
Column temperature: 25° C.

Example 1

Ready-to-Dilute Composition (60 mg/Vial) to be Diluted Before Injecting

| Ingredient | Amount |
|---|---|
| Carfilzomib | 60 milligrams |
| Ethanol | 5 milliliters |
| Propylene Glycol | 2.5 milliliters |
| Lactobionic Acid | 400 milligrams |

-continued

| Ingredient | Amount |
|---|---|
| Acetate Buffer (15 millimolar, pH 3.5) | 1 milliliter |
| Polysorbate 80 | 500 milligrams |
| 5% Dextrose | 0.5 milliliters |

The composition of Example 1 was prepared by placing 60 milligrams of carfilzomib in a compounding vessel. 5 milliliters of ethanol was then added to the compounding vessel and the contents of the compounding vessel were mixed. 2.5 milliliters propylene glycol was added to the compounding vessel and the contents of the vessel were again mixed. Next, 1 milliliter of 15 mM acetate buffer and 500 milligrams of Polysorbate 80 were added to the compounding vessel and the contents therein were mixed. 400 milligrams lactobionic acid was then added to the compounding vessel and the contents of the vessel were mixed until the lactobionic acid was dissolved. 0.5 milliliters of a 5% dextrose solution was then added to the compounding vessel and the contents therein were mixed. Once mixing was completed, the contents of the compounding vessel were filtered through a 0.22 micron PVDF filter.

Physicochemical data for the composition of Example 1 is shown below:

| Temperature | Time | Appearance | Assay (%) | RRT 0.82 | RRT 0.98 | RRT 1.02 | RRT 1.18 | Total |
|---|---|---|---|---|---|---|---|---|
| | T = 0 | CCS | 104.9 | — | 0.79 | 0.77 | — | 1.56 |
| 40° C./75% RH | 1 Week | CCS | 89.3 | 0.05 | 1.26 | 0.77 | — | 2.05 |
| | 2 Week | CCS | 113.4 | 0.57 | 2.11 | 0.85 | — | 3.53 |
| | 1 Month | CCS | 90.6 | 0.10 | 2.67 | 0.64 | 4.23 | 7.64 |
| | 3 Month | CCS | 44.64 | 0.28 | 4.07 | 0.28 | 16.15 | 20.78 |
| 25° C./60% RH | 1 Month | CCS | 105.8 | 0.15 | 1.11 | 0.77 | — | 2.03 |
| | 3 Month | CCS | 107.9 | 0.63 | 2.13 | 0.73 | 1.22 | 4.71 |

CCS = clear colorless solution
RRT = relative retention time

As can be seen from the physicochemical data, the composition of Example 1, which comprises lactobionic acid as well as ethanol and propylene glycol solvents, remained stable for an extended period of time even when stored at temperatures of 25° Celsius. The ready to dilute composition is stable at room temperature for at least 3 months.

Example 2

Ready-to-Dilute Composition (60 mg/Vial) to be Diluted Before Injecting

| Ingredient | Amount |
|---|---|
| Carfilzomib | 60 milligrams |
| Ethanol | 5 milliliters |
| PEG 300 | 2.5 milliliters |
| Lactobionic Acid | 400 milligrams |
| Acetate Buffer (15 millimolar, pH 3.5) | 1 milliliter |
| Polysorbate 80 | 500 milligrams |
| 5% Dextrose | 0.5 milliliters |

The composition of Example 2 was prepared by placing 60 milligrams of carfilzomib in a compounding vessel. 5 milliliters of ethanol was then added to the compounding vessel and the contents of the compounding vessel were mixed. 2.5 milliliters PEG 300 was added to the compounding vessel and the contents of the vessel were again mixed. Next, 1 milliliter of 15 mM acetate buffer, and 500 milligrams of Polysorbate 80, were added to the compounding vessel and the contents therein were mixed. 400 milligrams lactobionic acid was then added to the compounding vessel and the contents of the vessel were mixed until the lactobionic acid was dissolved. 0.5 milliliters of a 5% dextrose solution was then added to the compounding vessel and the contents therein were mixed. Once mixing was completed, the contents of the compounding vessel were filtered through a 0.22 micron PVDF filter.

Physicochemical data of the composition of Example 2 is shown below:

| Temperature | Time | Appearance | Assay (%) | RRT 0.82 | RRT 0.98 | RRT 1.02 | RRT 1.18 | Total |
|---|---|---|---|---|---|---|---|---|
| | T = 0 | CCS | 97.0 | — | 0.78 | 0.77 | — | 1.55 |
| 40° C./75% RH | 1 Week | CCS | 98.1 | 0.34 | 1.35 | 0.77 | — | 2.45 |
| | 2 Week | CCS | 87.0 | 0.66 | 1.96 | 0.71 | — | 3.33 |
| | 1 Month | CCS | 84.8 | 1.33 | 2.83 | 0.57 | 2.93 | 7.66 |
| | 3 Month | CCS | 53.0 | 0.22 | 4.19 | 0.37 | 8.74 | 13.52 |
| 25° C./60% RH | 1 Month | CCS | 106.0 | 0.22 | 1.14 | 0.75 | — | 2.08 |
| | 3 Month | CCS | 99.65 | 0.84 | 2.14 | 0.65 | 0.66 | 4.29 |

CCS = clear colorless solution
PPT = precipitate
RRT = relative retention time

As can be seen from the physicochemical data, the composition of Example 2, which comprises lactobionic acid as well the solvents ethanol and PEG 300, remained stable for an extended period of time even when stored at temperatures of 25° Celsius. The ready to dilute composition is stable at room temperature for at least 3 months.

Example 3

Ready-to-Use Composition (2 mg/mL)

| Ingredient | Amount |
| --- | --- |
| Carfilzomib | 60 mg |
| Ethanol | 12 mL |
| PEG 300 | 2.5 mL |
| Lactobionic Acid | 400 mg |
| Acetate Buffer (15 millimolar, pH 3.5) | 2 mL |
| Polysorbate 80 | 500 mg |
| 5% Dextrose | Q.S to 30 g |

The composition of Example 3 was prepared by placing 60 milligrams of carfilzomib in a compounding vessel. 12 milliliters of ethanol was then added to the compounding vessel and the contents of the compounding vessel were mixed. 2.5 milliliters PEG 3000 was added to the compounding vessel and the contents of the vessel were again mixed. Next, 2 mL of 15 mM acetate buffer and 500 milligrams of Polysorbate 80 were added to the compounding vessel and the contents therein were mixed. 400 milligrams lactobionic acid was then added to the compounding vessel and the contents of the vessel were mixed until the lactobionic acid was dissolved. A sufficient amount of 5% dextrose solution was then added to the compounding vessel so as to provide 30 g and the contents therein were mixed. Once mixing was completed, the contents of the compounding vessel were filtered through a 0.22 micron PVDF filter.

Physicochemical data for the composition of Example 3 is shown below:

| | | | | Impurities | | | | |
| --- | --- | --- | --- | --- | --- | --- | --- | --- |
| Temperature | Time | Appearance | Assay (%) | RRT 0.82 | RRT 0.98 | RRT 1.02 | RRT 1.18 | Total |
| | T = 0 | CCS | 107.5 | — | 0.85 | 0.77 | — | 1.61 |
| 40° C./75% RH | 1 Week | CCS | 100.9 | 0.47 | 1.7 | 0.77 | — | 2.91 |
| | 2 Week | CCS | 96.2 | 0.82 | 2.47 | 0.75 | | 4.03 |
| | 1 Month | CCS | 88.4 | 1.79 | 3.75 | 0.6 | — | 6.15 |
| | 2 Month | CCS | 105.5 | 0.39 | 1.21 | 0.64 | — | 2.23 |
| 25° C./60% RH | 1 Month | CCS | 108.1 | 0.48 | 1.32 | 0.75 | — | 2.55 |
| | 2 Month | CCS | 99.31 | 0.96 | 2.53 | 0.56 | — | 4.04 |
| | 3 Month | CCS | 97.46 | 1.07 | 2.70 | 0.55 | — | 4.31 |
| 4° C. | 2 Month | CCS | 113.17 | 0.41 | 1.33 | 0.69 | — | 2.43 |
| | 3 Month | CCS | 108.29 | — | 0.79 | 0.66 | — | 1.44 |

CCS = clear colorless solution
RRT = relative retention time

The ready to use composition is stable at room temperature for at least 3 months.

The preceding examples, and exemplary language, are merely illustrate and should not be construed to limit the scope of the invention discussed herein, unless otherwise claimed. In addition, no language in the specification should be construed as indicating any non-claimed element as essential to the practice of the invention. For instance, while particular embodiments of the present invention have been illustrated and described, it should be apparent to those skilled in the art that various other changes and modifications can be made without departing from the spirit and scope of the invention. For instance, all methods described herein can be performed in any suitable order unless otherwise indicated herein or otherwise clearly contradicted by context.

What is claimed is:

1. A ready to use, multi-dose liquid pharmaceutical composition suitable for injection, comprising:
   (i) a liquid formulation comprising a non-volatile sugar acid, and carfilzomib or a pharmaceutically acceptable salt thereof;
   (ii) wherein the liquid formulation comprises a solvent system suitable for injection and including at least one of ethanol, propylene glycol, polyethylene glycol, and water;
   (iii) wherein the weight ratio of the non-volatile sugar acid to the carfilzomib or the pharmaceutically acceptable salt thereof ranges from 2:1 to 15:1; liquid formulation is present in a container in a quantity suitable for at least two independent and distinct administrations; and
   (iv) wherein the liquid formulation is formulated to maintain degradation of the carfilzomib or the pharmaceutically acceptable salt thereof at a level of less than 10% when the liquid formulation is stored over at least one month at 25 degrees Celsius and 60% relative humidity.

2. The pharmaceutical composition of claim 1, wherein the non-volatile sugar acid is selected from the group consisting of lactobionic acid, glycolic acid, malic acid, citric acid, lactic acid, mandelic acid, and tartaric acid.

3. The pharmaceutical composition of claim 1, wherein the solvent system comprises ethanol and propylene glycol.

4. The pharmaceutical composition of claim 1, wherein the solvent system comprises ethanol and polyethylene glycol.

5. The pharmaceutical composition of claim 1, wherein the non-volatile sugar acid is lactobionic acid.

6. The pharmaceutical composition of claim 5, wherein the concentration of the carfilzomib or the pharmaceutically acceptable salt thereof in the solvent system ranges from about 0.1 to about 10.0 mg/mL and the weight ratio of the carfilzomib or the pharmaceutically acceptable salt thereof to lactobionic acid ranges from about 2:1 to 15:1.

7. The pharmaceutical composition of claim 6, wherein the solvent system comprises ethanol, propylene glycol, and water.

8. The pharmaceutical composition of claim 6, wherein the solvent system comprises ethanol, polyethylene glycol, and water.

9. The pharmaceutical composition of claim 1, wherein:
(i) the non-volatile sugar acid is lactobionic acid, and wherein the weight ratio of the lactobionic acid to carfilzomib or the pharmaceutically acceptable salt thereof ranges from about 2:1 to 15:1; and
(ii) the solvent system includes ethanol, propylene glycol, and water, and wherein the ethanol and propylene glycol comprise more than about 50% (v/v) of the solvent system, wherein the concentration of the carfilzomib or the pharmaceutically acceptable salt thereof ranges from about 1 mg/mL to about 6 mg/mL.

10. The pharmaceutical composition of claim 1 wherein:
(i) the non-volatile sugar acid is lactobionic acid, and wherein the weight ratio of the lactobionic acid to carfilzomib or the pharmaceutically acceptable salt thereof ranges from about 4:1 to 7:1; and
(ii) the solvent system includes ethanol, polyethylene glycol, and water, and wherein the ethanol and polyethylene glycol comprise more than about 50% (v/v) of the solvent system, wherein the concentration of the carfilzomib or the pharmaceutically acceptable salt thereof ranges from about 1 mg/mL to about 6 mg/mL.

11. The pharmaceutical composition of claim 1, wherein the liquid formulation is formulated to be stable at room temperature for at least 3 months.

12. A ready to dilute, multi-dose liquid pharmaceutical composition, comprising:
(i) a liquid formulation comprising a non-volatile sugar acid and carfilzomib or a pharmaceutically acceptable salt thereof, wherein the weight ratio of the non-volatile sugar acid to the carfilzomib or the pharmaceutically acceptable salt thereof ranges from 2:1 to 15:1;
(ii) wherein the liquid formulation comprises a solvent system suitable for injection upon dilution with a suitable diluent, the solvent system including at least one of ethanol, propylene glycol, polyethylene glycol, and water;
(iii) wherein the liquid formulation is present in a container in a quantity suitable for at least two independent and distinct administrations; and
(iv) wherein the liquid formulation is formulated to maintain degradation of the carfilzomib or the pharmaceutically acceptable salt thereof at a level of less than 10% when the liquid formulation is stored over at least one month at 25 degrees Celsius and 60% relative humidity.

* * * * *